United States Patent [19]

Durand et al.

[11] Patent Number: 5,723,635
[45] Date of Patent: Mar. 3, 1998

[54] PROCESS FOR THE PURIFICATION OF TAXOIDS

[75] Inventors: André Durand, Sainte-Geneviève-des-Bois; Alain Gerbaud, Athis-Mons; Rodolphe Margraff, Viry-Châtillon, all of France

[73] Assignee: Rhone-Poulenc Rorer S.A., Antony, France

[21] Appl. No.: 522,418

[22] PCT Filed: Mar. 18, 1994

[86] PCT No.: PCT/FR94/00300

§ 371 Date: Sep. 21, 1995

§ 102(e) Date: Sep. 21, 1995

[87] PCT Pub. No.: WO94/21622

PCT Pub. Date: Sep. 29, 1994

[30] Foreign Application Priority Data

Mar. 22, 1993 [FR] France ................... 93 03251

[51] Int. Cl.$^6$ .................................................. C07D 305/14
[52] U.S. Cl. ............................................. 549/510; 549/511
[58] Field of Search ............................. 549/510, 511

[56] References Cited

U.S. PATENT DOCUMENTS

| 4,814,470 | 3/1989 | Colin et al. ............... 514/449 |
| 4,924,012 | 5/1990 | Colin et al. ............... 549/510 |

FOREIGN PATENT DOCUMENTS

| 0 253 738 | 1/1988 | European Pat. Off. . |
| 0 336 841 | 10/1989 | European Pat. Off. . |
| WO 92/09589 | 6/1992 | WIPO . |

OTHER PUBLICATIONS

Voegelein et al, J. Med. Chem., 34(3), pp. 992–998, 1991.
A. Foucault et al., "La chromatographie a contre–courant", Analusis, vol. 16, No. 3, (1988), pp. 157–167.
Tian–You Zhang et al., "Rapid Separation Of Flavonoids By Analytical High–Speed Counter–Current Chromatography", Journal of Chromatography, 445, (1988), pp. 199–206 (abstract).
Yoichiro Ito et al., "Improved Cross–Axis Synochronous Flow–Through Coil Planet Centrifuge For Performing Counter–Current Chromatography", Journal of Chromatograpy, 463, (1988), pp. 305–316 (abstract).
Molina Bhatnagar et al., "Improved Cross–Axis Synchronous Flow–Through Coil Planet Centrifuge For Performing Counter–Current Chromatography", Journal of Chromatography, 463, (1989), pp. 317–328 (abstract).
Yoichiro Ito et al., "Horizontal Flow–Through Coil Planet Centrifuge Equipped With A Set Of Multilayer Coils Around The Column Holder", Journal of Chromatography, 457, (1988), pp. 393–397 (abstract).
Takashi Yoshida et al., "Chromatography Of Tannis", Journal of Chromatography, 467 (1989), pp. 139–147 (abstract).
Hisao Oka et al., "Improved Method For Continuous UV Monitoring In High–Speed Counter–Current Chromatography", Journal of Chromatography, 475, (1989), pp. 229–235 (abstract).
Nabil Tayar et al., "Use Of Centrifugal Partition Chromatography For Assessing Partition Coefficients In Various Solvent System", Journal of Chromatography, 469, (1989), pp. 91–99 (abstract).
Hisao Oka et al., "Multilayer Coil Planet Centrifuge For Analytical High–Speed Counter–Current Chromatography", Journal of Chromatography, 479, (1989), pp. 53–60 (abstract).
Yoichiro Ito et al., "Improved High–Speed Counter–Current Chromatograph With Three Multilayer Coils Connected In Series, Journal of Chromatography", 475, (1989), pp. 219–277 (abstract).
R. Vanhaelen et al., "High Speed Countercurrent Chromatography Separation Of Taxol And Related Di Terpenoids From Taxus Baccata", Journal Of Liquid Chromatography, vol. 15, No. 4, (1992) pp. 697–706.
S. Harvey et al., "Separation of Taxol From Related Taxenes In Taxus Brevifola Extracts By Isocratic Elution Reversed–Phase High–Performance Liquid Chromatography", Journal Of Chromatography, vol. 587, (1991) pp. 300–305.

*Primary Examiner*—Ba K. Trinh
*Attorney, Agent, or Firm*—Finnegan, Henderson, Farabow, Garrett & Dunner, L.L.P.

[57] ABSTRACT

A method for purifying 10-deacetylbaccatin III by centrifugal partition chromatography with aliphatic ketone and water as solvent mixture.

5 Claims, No Drawings

5,723,635

PROCESS FOR THE PURIFICATION OF TAXOIDS

This application is a 371 of PCT/FR 94/0030, dated Mar. 18, 1994.

The present invention relates to a process for the purification of taxoids by centrifugal partition chromatography.

More especially, the present invention relates to a process for the purification of Taxotere and of 10-deacetylbaccatin III.

10-Deacetylbaccatin III extracted from yew leaves is useful in the preparation of Taxotere under the conditions described, for example, in European Patents EP 0,253,738 or EP 0,336,841 or in International PCT WO 92/09,589.

10-Deacetylbaccatin III obtained by extraction of yew leaves contains, depending on the species from which it originates, impurities which are chiefly products belonging to the taxoid family, such as, for example, 2α-benzoyloxy-4-acetoxy-5β,20-epoxy-1β,7β,10β,13α,19-pentahydroxy-9-oxo-11-taxene, 2α-benzoyloxy-4-acetoxy-5β,20-epoxy-1β, 7α,10β,13α-tetrahydroxy-11-taxene or taxins.

Taxotere which is obtained by partial synthesis from 10-deacetylbaccatin III contains as chief impurities the esterification products of the impurities contained in 10-deacetylbaccatin III, as well as other impurities originating, for example, from the epimerization of the carbon at position 2' of the side chain.

10-Deacetylbaccatin III and Taxotere itself may generally be purified by liquid chromatographic methods on a column, and more especially by high performance liquid chromatography (HPLC) on a silica column. However, while these methods are especially well suited to the purification of a few tens of grams, their industrial extrapolation comes up against constraints, such as the quantity of solvents consumed and the handling and destruction of the (silica) support contaminated by toxic residues, which become paramount.

In the case of taxoids which constitute products whose toxicity is often very high and whose lability is great, it is especially important to have the possibility of using purification methods which have good productivity, which do not require a solid support which is expensive to buy, use and destroy, which require the use of small quantities of solvents and which can be readily automated to permit continuous production.

It has now been found, and this forms the subject of the present invention, that the purification of taxoids, and more especially the purification of Taxotere and of 10-deacetylbaccatin III, may be achieved by carrying out centrifugal partition chromatography (CPC) or high speed countercurrent chromatography, the principle of which is described, for example, by A. Foucault and P. Rosset, Analusis, 16 (3), 157–167 (1988).

Centrifugal partition chromatography makes it possible to effect partition of the constituents of the mixture to be separated between two immiscible liquid phases, by establishing successive equilibria produced in a logical manner and automatically.

This method is characterized by a very efficient partition mechanism, a strong retention of the stationary phase and a high speed of the mobile phase, leading to excellent separations in a few hours.

Centrifugal partition chromatography requires the use of two or more solvents supplying 2 partially miscible phases. Although there is an unlimited number of solvents displaying this feature, it is especially important industrially to use non-chlorinated and non-toxic industrial solvents. Among solvents which may be used industrially incurring lower risks, alcohols such as methanol, ethers such as methyl t-butyl ether, esters such as ethyl acetate, ketones such as methyl isobutyl ketone and aliphatic hydrocarbons such as heptane or isooctane may be mentioned.

To carry out an efficient purification, it is necessary to choose a mixture of solvents whose rapid and complete separation yields two phases for which the partition coefficient is between 0.1 and 10, and preferably between 0.5 and 5, and still more especially in the vicinity of 1.

A product for which the partition coefficient (K) is, for example, equal to 10 is 10 times more soluble in the upper phase than in the lower phase. Consequently, it will be eluted very rapidly if the upper phase is mobile, and after a very long time, with a poor resolution, if the lower phase is the one which is mobile. In contrast, when K is in the region of 1, the solubility will be practically identical in both phases, and both modes of elution may be used, and where appropriate combined, to obtain maximum resolution.

In the particular case of 10-deacetylbaccatin III, mixtures of an aliphatic hydrocarbon, an ester, an alcohol and water such as a heptane/ethyl acetate/methanol/water (1:2:1:2 by volume) mixture, and more especially mixtures of aliphatic ketones and water such as a methyl isobutyl ketone/acetone/water (2:3:2 by volume) mixture, are most especially suitable.

Furthermore, it is necessary for the retention in the stationary phase, which is the fraction of the total volume of the apparatus occupied by the stationary phase at equilibrium, the flow rate of the mobile phase being fixed, to be as high as possible and equal to at least 50%.

Furthermore, in order to improve the productivity, it is especially advantageous to be able to work at a high flow rate, which is limited by the maximum pressure imposed by the rotor.

In the particular case of Taxotere, it is advantageous to use a mixture of an aliphatic hydrocarbon, an ester, an alcohol and water, such as a heptane/ethyl acetate/methanol/water (2:4:3:2 by volume) system, which has a retention of 80% and a partition coefficient in the region of 0.5, thus giving a narrower peak which is eluted rapidly, thereby leading to a very marked improvement in productivity.

The centrifugal partition chromatography may be carried out in any commercially available apparatus suitable for this purpose, such as those which have been developed by Yoichiro Ito [CRC Crit. Rev. Anal. Chem., 17, 65 (1986)] or marketed by SANKI Engineering Limited in Kyoto (Japan).

The present invention also relates to purified Taxotere and purified 10-deacetylbaccatin III when they are obtained by carrying out the process according to the invention.

The examples which follow show how the invention may be put into practice.

EXAMPLE 1

Purification of Taxotere

Taxotere (or 4-acetoxy-2α-benzoyloxy-5β,20-epoxy-1α, 7β,10β-trihydroxy-9-oxo-11-taxen-13α-yl (2R,3S)-3-t-butoxycarbonylamino-3-phenyl-2-hydroxypropionate) is obtained by treatment of 4-acetoxy-2α-benzoyloxy-5β,20-epoxy-1β-hydroxy-7β,10β-bis(2,2,2-trichloroethoxycarbonyloxy)-9-oxo-11-taxen-13α-yl)(2R,3S)-3-t-butoxycarbonylamino-3-phenyl-2-hydroxypropionate with zinc in the presence of acetic acid under the conditions described in European Patent EP 0,336,841.

10 g of 4-acetoxy-2α-benzoyloxy-5β,20-epoxy-1β-hydroxy-7β,10β-bis(2,2,2-trichloroethoxycarbonyl-oxy)-9-oxo-11-taxen-13α-yl (2R,3S)-3-t-butoxycarbonyl-amino-3- phenyl-2-hydroxypropionate are dissolved in 150 cm³ of methyl t-butyl ether, and 10 g of zinc are then added. After evaporation to dryness, a grey powder is obtained, which is placed in a reactor.

After stirring, a mixture of 6 cm³ of acetic acid and 50 cm³ of acetonitrile is added in the course of 5 minutes. The mixture is heated externally with a water bath at 45° C. for 1 hour. After cooling in an ice bath, 850 cm³ of methyl t-butyl ether are introduced with vigorous stirring, and the zinc salts and excess zinc ate then filtered off on sintered glass of porosity 4.

The filtrate is concentrated to dryness. A foam (12 g) is thereby obtained, which is taken up immediately in 20 cm³ of ethyl acetate, 15 cm³ of methanol, 10 cm³ of heptane and 10 cm³ of water.

Centrifugal partition chromatography is performed on a SANKI LLI-07 apparatus. The centrifuge is fed by 2 piston pumps equipped with poppet valves limiting the pressure to 55 bars. One pump serves to convey one or other of the two phases by means of a selector valve; the other pump is reserved for injection.

After filling of the apparatus with stationary phase at a low speed of rotation (200 rpm) and high flow rate (110 cm³/minute), injection is performed immediately.

The two phases are injected, beginning with the aqueous phase, and elution is performed at a flow rate of 60 cm³/minute with the aqueous phase of the hexane/ethyl acetate/methanol/water (2:4:3:2 by volume) system. 1.9 liters of stationary phase are collected, equivalent to a 71% retention, and 15-cm³ fractions are then collected. Fractions 72 to 110 are pooled and concentrated to a volume of 140 cm³. The precipitate formed is separated by filtration. 5.2 g of Taxotere trihydrate, assaying at 99.7% using internal standardization, are thereby obtained in an 80.5% yield.

EXAMPLE 2

Purification of Taxotere

Using the procedure described in Example 1, but starting with 82 g of 4-acetoxy-2α-benzoyloxy-5β,20-epoxy-1β-hydroxy-7β,10β-bis(2,2,2-trichloroethoxycarbonyloxy)-9-oxo-11-taxen-13α-yl (2R,3S)-3-t-butoxycarbonylamino-3-phenyl-2-hydroxypropionate, 82 g of zinc and 150 cm³ of a mixture of 49.2 cm³ of acetic acid and 328 cm³ of acetonitrile, 115 g of crude product theoretically containing 49.69 g of Taxotere or 53 g of Taxotere trihydrate are obtained.

The crude product is taken up with 450 cm³ of methyl t-butyl ether and then washed 3 times with, in total, 450 cm³ of water containing 15 g of sodium chloride. The combined aqueous phases are extracted with twice 200 cm³ of methyl t-butyl ether. The three ether extracts are combined and concentrated to dryness. 72 g of a foam are thereby obtained, which product is taken up with 120 cm³ of methanol.

To the pale yellow solution obtained, there are added, in order, 160 cm³ of ethyl acetate, 80 cm³ of water and 80 cm³ of heptane.

Two clear liquid phases of total volume 460 cm³ are thereby obtained, the upper layer of which represents only ¼ of the total volume instead of 35% in the absence of Taxotere.

The centrifugal partition chromatography apparatus is filled with the organic phase at a flow rate of 110 cm³/minute with a speed of rotation of 200 rpm. When the apparatus is full, the speed of rotation is raised to 800 rpm. The aqueous phase is injected and then, after injection of the organic phase, rinsing is performed with 200 cm³ of organic phase and then elution, at a flow rate of 60 cm³/minute, with the aqueous phase.

2.5 liters of excess stationary phase are collected, equivalent to a 67.7% retention.

After 200 cm³ of aqueous mobile phase have been passed through, 360 12- to 13-cm³ fractions are collected. Fractions 25 to 110, concentrated to a volume of 200 cm³, give, in an 87.7% yield, a precipitate of 46.5 g of Taxotere trihydrate, the purity of which is 99.1%.

EXAMPLE 3

Purification of 10-deacetylbaccatin III

Centrifugal partition chromatography is performed on a SANKI HPCPC series 1000 chromatograph of total volume 245 cm³.

The rotor rotating at 100 rpm is filled in the descending mode by simultaneously pumping in the organic phase, at a flow rate of 6 cm³/minute, and the aqueous phase, at a flow rate of 3 cm³/minute, of a methyl isobutyl ketone/acetone/water (2:3:2 by volume) mixture.

The speed of rotation is thereafter raised to 1200 rpm, and 1.5 g of crystallized crude 10-deacetylbaccatin III, containing 83.3% of 10-deacetylbaccatin III and 3.4% of 10-deacetyl-19-hydroxybaccatin III, is then injected in.

Elution is then performed in the descending mode with the aqueous phase at a flow rate of 3 cm³/minute, collecting 6-cm³ fractions every 2 minutes.

The 10-deacetyl-19-hydroxybaccatin III is contained in fractions 39 to 52.

At the 61st fraction, the direction of elution is reversed, then using the organic phase as mobile phase in the ascending mode at a flow rate of 5 cm³/minute and collecting 10-cm³ fractions every 2 minutes.

Fractions 70 to 84, which contain the 10-deacetylbaccatin III, are concentrated under reduced pressure. After recrystallization in 15 cm³ of acetonitrile, 1.25 g of 10-deacetylbaccatin III solvated with acetonitrile (1 mol/mole) are obtained in the form of white crystals, the purity of which, determined by HPLC using internal standardization, is 98%.

The yield, corrected, is 91.2%.

We claim:

1. A process for the purification of 10-deacetylbaccatin III by centrifugal partition chromatography, said process comprising
   centrifuging in a suitable centrifugal partition chromatography apparatus, for a time sufficient to purify said 10-deacetylbaccatin III, impure 10-deacetylbaccatin III and at least two solvents which are capable of forming two partially miscible phases, wherein said two solvents are a mixture of at least one aliphatic ketone and water, and wherein the partition coefficient between the two partially miscible phases ranges from 0.1 to 10.

2. The process of claim 1, wherein said at least two solvents are a mixture of methyl isobutyl ketone, acetone, and water.

3. The process of claim 2, wherein said solvents are methyl isobutyl ketone/acetone/water in a ratio of 2:3:2 by volume.

4. The process of claim 1, wherein the partition coefficient between the two partially miscible phases ranges from 0.5 to 5.0.

5. The process of claim 4, wherein the partition coefficient between the two partially miscible phases is about 1.

\* \* \* \* \*